Figure 1:
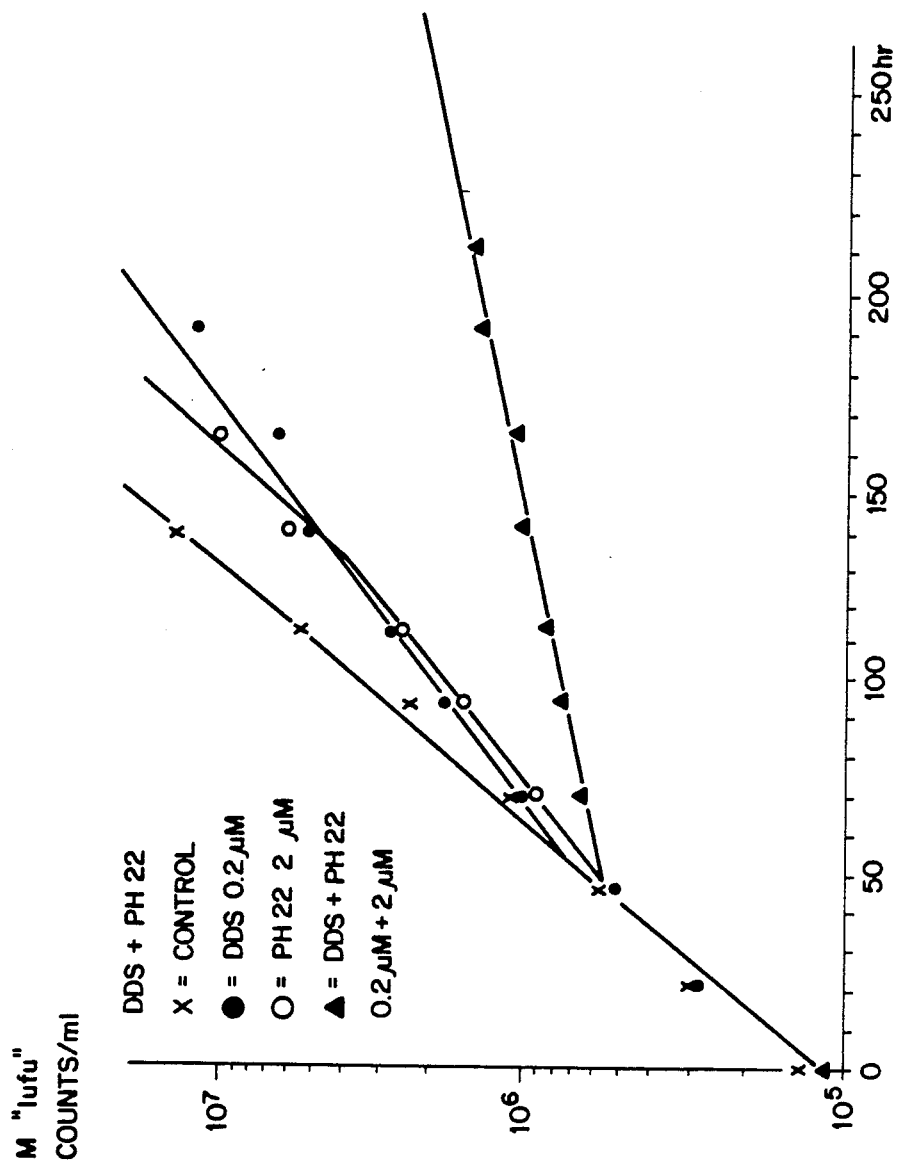

United States Patent [19]

Schaper et al.

[11] Patent Number: 4,997,835
[45] Date of Patent: Mar. 5, 1991

[54] SUBSTITUTED 2-ACYLPYRIDINE-α-(N)-HETARLYHYDRAZONES AND MEDICAMENTS CONTAINING THE SAME

[76] Inventors: Klaus-Jürgen Schaper, Parkallee 39c; Joachim K. Seydel, Mühloh 2, both of 2061 Borstel, Fed. Rep. of Germany

[21] Appl. No.: 348,583
[22] PCT Filed: May 14, 1988
[86] PCT No.: PCT/DE88/00289
§ 371 Date: Mar. 7, 1989
§ 102(e) Date: Mar. 7, 1989
[87] PCT Pub. No.: WO88/08842
PCT Pub. Date: Nov. 17, 1988

[30] Foreign Application Priority Data

May 14, 1987 [DE] Fed. Rep. of Germany ....... 3716131

[51] Int. Cl.$^5$ .................. A61K 31/50; C07 401/12
[52] U.S. Cl. ..................... 514/248; 514/252; 514/275; 514/313; 514/343; 514/253; 514/310; 544/237; 544/238; 544/328; 544/331; 546/264; 546/159
[58] Field of Search ..................... 514/252, 248

[56] References Cited

U.S. PATENT DOCUMENTS 3,433,871  3/1969  Johnston ............................ 514/252
4,670,437  6/1987  Abdulla ............................. 514/252

FOREIGN PATENT DOCUMENTS 3716131  11/1988  Fed. Rep. of Germany .
0014579   1/1982  Japan ................................. 514/248
8808842  11/1988  World Int. Prop. O. .

OTHER PUBLICATIONS

Shapiro et al., Jour. Protozool. vol. 29, No. 1, pp. 85–90, (1982).
Bell et al., Org. Mag. Resonance vol. 7, pp. 512–519, (1975).
Pellerano et al., Il Farmaco, vol. 40, No. 9, pp. 645–654, (1985).
Miakelson, Jour. Inorg. Nucl, Chen., vol. 43, pp. 123–126, (1981).
Pellerano et al., Chem. Abst. vol. 91, Entry 175157n, (1979).
Chem. Abstr. vol. 84, Entry 58093n, (1976), Bell et al.

Primary Examiner—Donald G. Daus
Attorney, Agent, or Firm—Nixon & Vanderhye

[57] ABSTRACT

Substituted 2-acylpyridine-α-(N)-hetarylhydrazones are described, which are suitable as active substances for the treatment of antimicrobial and in particular antimycobacterial diseases, as well as active substances for the treatment of malaria or malignant tumours. The compounds have a marked synergistic activity combined with inhibitors of folate synthase, dihydrofolic acid reductase, DNA-synthesis and RNA-synthesis.

9 Claims, 1 Drawing Sheet

SUBSTITUTED 2-ACYLPYRIDINE-α-(N)-HETARLYHYDRAZONES AND MEDICAMENTS CONTAINING THE SAME

DESCRIPTION

The invention relates to substituted 2-acylpyridine-α-(N)-hetarylhydrazones, their preparation and their use as medicaments for the treatment of microbial and in particular mycobacterial infections, as well as malaria and malignant tumours.

The pharmaceutical activity of heterocyclic substituted 2-acylpyridines is known. Thus, compounds of the 2-acylpyridine-thiosemicarbazone type have a pharmaceutical activity in the treatment of bacterial and in particular mycobacterial diseases, such as leprosy and tuberculosis. They are also suitable as agents for the treatment of malaria and malignant tumours.

However, the high toxicity of these compounds is disadvantageous. Thus, for example, K. C. Agrawal et al in Biochem. Pharmacol, 23, pp. 2421–2429, 1974 reports on the serious gastrointestinal toxicity of 5-hydroxypyridine-2-(carbox)-aldehyde-thiosemicarbazone, a compound having antileukemic activity. Inter alia L. Weinstein in Pharmacol. Basis Ther, 5th edition, pp. 1201 to 1223, 1973 refers to the anorexia, nausea and vomiting effects caused by thiosemicarbazones and their derivatives in general.

Therefore the problem of the present invention is to provide novel compounds and pharmaceutical active substances, whose activity is superior to that of compounds of the 2-acylpyridine-thiosemicarbazone type, whilst simultaneously reducing the toxicity.

To solve this problem, the novel substituted 2-acylpyridine-α-(N)-hetarylhydrazones of general formula I

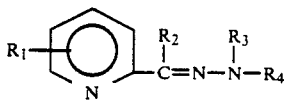

I are proposed, in which $R_1$ stands for hydrogen, halogen, an alkyl group with 1 to 8 C-atoms, a benzyloxy; benzo, amino, or acetamino group, $R_2$ hydrogen, an alkyl group with 1 to 8 C-atoms, an amino or a phenyl group, $R_3$ hydrogen or an alkyl group with 1 to 3 C-atoms and $R_4$ a radical of general formulas II, III or IV

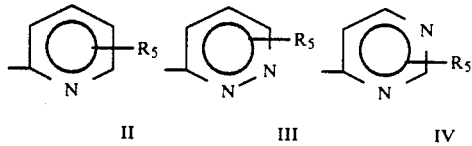

II  III  IV in which $R_5$ stands for hydrogen, halogen, an alkyl or alkoxy group with 1 to 4 C-atoms, a benzo group or a dialkylamino or substituted dialkylamino group with 1 to 3 C-atoms in the alkyl radicals, in which a. at least one of the substituents $R_1$ to $R_3$ and $R_5$ is not hydrogen if $R_4$ is a pyridyl radical,
b. at least one of the substituents $R_1$ to $R_3$ is not hydrogen, if $R_4$ is a pyridyl radical and $R_5$ are 3′, 4′-benzo, 5′, 6′-benzo or 6′-methyl groups,
c. at least one of the substituents $R_1$, $R_3$ and $R_5$ is not hydrogen if $R_4$ is a pyridyl radical and $R_2$ a phenyl group,
d. at least one of the substituents $R_2$, $R_3$ and $R_5$ is not hydrogen if $R_4$ is a pyridyl radical and $R_1$ is a 5 or 6-methyl group or a 3,4-benzo group,
e. at least one of the substituents $R_1$, $R_3$ or $R_5$ is not hydrogen if $R_2$ is an amino or methyl group,
f. at least one of the substituents $R_1$ or $R_5$ is not hydrogen if $R_2$ is methyl, $R_4$ is a pyridyl radical and $R_5$ is a 5′, 6′-benzo group, as well as medicaments according to claims 35 to 42. Preferred compounds are given in the subclaims.

Inventively it has been surprisingly found that the introduction of the α-(N)-hetaryl group in place of the thioamide group in combinations of the 2-acylpyridine-thiosemicarbazone type leads to a dramatic reduction in the toxicity with respect to mammals, whilst maintaining or increasing the pharmaceutical activity (cf. Table 1).

TABLE 1

| Acute toxicity of PH22(I) pyridine-2-aldehyde-TSC(11) and thiacetazone (III) in the case of rats and mice. | | |
| --- | --- | --- |
| | $LD_{50}$ (mg/kg body weight) | |
| I | >2000 | Rat. subc. |
| II | 30 | Rat. subc. |
| II | 40 | Mouse i.p. |
| (Cancer Res. 25, 1454 (1965) | | |
| III | 1000–2000 | Mouse. subc. |
| (J. Pharm. Pharmacol. 2, 764 (1950) | | |
| III | 950 | Mouse, p.o. |
| (Comptes Rendus Soc. Biol. 1310 (1950) | | |

The compounds according to the invention can be prepared in that in per se known manner the corresponding substituted pyridine aldehydes or ketones are reacted with the corresponding hydrazines.

The activity of the inventive compounds as growth inhibitors for in particular mycobacteria, as well as for malaria parasites and tumour cells was proved in that the minimum inhibitory concentration (MIC) and the concentration necessary for a semimaximum propagation rate inhibition ($I_{50}$) were determined using typical representatives of the inventive compounds.

For inhibiting the growth of various mycobacteria strains, there was a 5 to 200 times increased activity of the inventive compounds compared with commercially available products (cf. Table 2).

There was also found to be a synergistic effect of combinations of the claimed compounds with inhibitors of folate synthase, such as sulphones or sulphonamides, dihydrofolic acid reductase such as methotrexate, brodimoprim or 2,4-diamino-5-{4-[2-(4′-aminophenyl-4-sulphonyl phenylamino)-ethoxy]-3,5-dimethoxybenzyl}-pyrimidine, hereinafter referred to as K 107 and 2,4-diamino-5-{4-[3-(4′-aminophenyl-4-sulphonyl phenylamino)-propoxy]-3,5-dimethoxybenzyl}-pyrimidine, hereinafter referred to as K 130, as well as with inhibitors of DNA-synthesis, such as e.g. 5-F-uracil, guanazol or desferal, as well as with inhibitors of RNA-polymerase (e.g. rifampicin). This effect is noticeable both in inhibiting mycobacterial growth and in inhibiting the growth of malaria plasmodia (cf. Tables 3 to 16, 18 and 20).

The synergistic effectiveness can be further increased if the inventive compounds are simultaneously combined with inhibitors of different types (cf. Table 4). The significance of the inventive compounds and medicaments is also inter alia based on the possibility of treating partly resistant mycobacteria or malaria parasites or reducing the resistance development in monotherapy. The effectiveness, particularly in combinations, with respect to microbacterial problem germs, such as e.g. M. avium (patient strain, Tables 2 and 15) must also be stressed.

The compounds according to the invention in vitro have a marked cytostatic activity on the human mammary tumour cell line MDA-MB231 (Table 21).

The above-described, pharmaceutical activities were not only found in the case of the novel inventive compounds but, surprisingly, also in the case of the already known compounds pyridine-2-aldehyde-2'-quinolylhydrazone, hereinafter called PQ 22, pyridine-2-aldehyde-2'-pyridylhydrazone, hereinafter called PH 22, 2-acetylpyridine-2'-pyridylhydrazone, hereinafter called PH 22-2, 2-acetylpyridine-2'-pyridyl-2'-quinolylhydrazone, hereinafter called PH 22-4, 2-benzoyl pyridine-2'-pyridylhydrazone, hereinafter called PH 22-9, 6-methyl pyridine-2-aldehyde-pyridylhydrazone, hereinafter called PH 22-10, pyridine-2-carboxylic acid 2'-pyridyl-amidrazone, hereinafter called PH 22-12, 5-methyl-2-aldehyde-pyridylhydrazone, hereinafter called PH 22-21, pyridine-2-aldehyde-1'-isoquinolylhydrazone, hereinafter called PH 22-27, pyridine-2-aldehyde-2'-(6'-methyl)-pyridylhydrazone, hereinafter called PH 22-31 and isoquinoline-1-aldehyde-2'-pyridyl hydrazone, hereinafter called PH 22-37 (cf. Tables 1 to 21).

Compounds PH 22-2, PH 22-4, PH 22-9 and PH 22-10 were described by C. Pellerano et al in Il Farmaco, Ed. Sci. 40, 645-654, 1985 and their suitability for the in vivo treatment of lymphatic leukaemia P388 was investigated. This publication indicated that the compounds were ineffective.

The inventive medicaments contain the aforementioned active substances or active substance combinations together with a compatible pharmaceutical carrier. This carrier can be an organic or inorganic carrier material suitable for enteral, percutaneous and parenteral administration, such as e.g. water, gum arabic, lactose, starch, magnesium stearate, tallow, vegetable oils, polyalkylene glycols, vaseline and the like. The preparations can also contain other pharmaceutically active substances, such as antipyretics, analgesics, antiphlogistics, etc. The pharmaceutical preparations can be administered orally, e.g. in the form of tablets, capsules, pills, powders, granules, solutions, syrups, suspension, elixirs, etc. However, administration can also take place parenterally, e.g. in the form of sterile solutions, suspensions or emulsions, or locally in the form of solutions, suspensions, ointments, powders, aerosols, etc.

The pharmaceutical preparations can also be sterilized and/or contain components such as preservatives, stabilizers, wetting agents, emulsifiers, salts and buffer substances.

The invention is illustrated hereinafter by means of examples.

EXAMPLE 1

Preparation of pyridine-2-aldehyde-1'-phthalazinylhydrazone (PH 22-1)

0.848 g of 1-hydrazinophthalazine.HCL were dissolved at 50° C. in 20 ml of a mixture of ethanol and water (1:1). An equivalent quantity of 1N NaOH and then an equivalent quantity of pyridine-2-aldehyde (0.46 g) in 10 ml of ethanol/H$_2$O were added. The mixture was refluxed for 20 minutes and then cooled. By carefully adding water, the substance was precipitated from the solution.

1.07 g of yellow, crystalline substance with a melting point of 193°-194° C. was obtained.

EXAMPLE 2

Preparation of 2-acetylpyridine-1'-phthalazinylhydrazone (PH 22-3)

0.5 g of 2-acetylpyridine was dissolved in 50 ml of water/methyl alcohol (1:1) and subsequently 0.82 g of 1-hydrazinophthalazine.HCL and 4.2 ml of 1N NaOH were added. The mixture was refluxed for 1.5 hours and then cooled. A crystalline substance precipitated, which was recrystallized from ethanol/water.

There was a 0.8 g yield of a yellow substance with a melting point of 191° to 195° C.

EXAMPLE 3

Preparation of 5-ethylpyridine-2-aldehyde-1'-phthalazinylhydrazone (PH 22-5)

2 g of 5-ethylpyridine-2-aldehyde, prepared in the manner indicated in Example 8, were dissolved in 30 ml of water. 2.2 g of 1'-hydrazinophthalazine hydrochloride and 4.4 ml of 1N NaOH in 20 ml of methanol were added to the solution. The mixture was refluxed for 2 hours, the activated carbon was then added and filtration took place in the hot state. The substance precipitated as oil, which crystallized after 48 hours. Recrystallization took place from ethanol/water.

There was a 0.81 g yield of a yellow substance with a melting point of 149° to 151° C.

EXAMPLE 4

Preparation of 5-benzyloxypyridine-2-aldehyde-1'-phthalazinylhydrazone (PH 22-6)

3.3 g of sodium were dissolved in 60 ml of methanol and stirred with 15 g of 5-hydroxy-2-methylpyridine in 230 ml of DMSO for 1 hour at a temperature of 80° to 90° C. The methanol was spun or rotated out after cooling the mixture. 23.5 g of benzylbromide were then added, followed by stirring for 20 hours at room temperature. The reaction mixture was then acidified with 2N HCL and mixed with 1500 ml of water. The mixture was then extracted with diethyl ether and the ether phase was discarded. The pH-value of the aqueous phase was then adjusted to approximately 8 and the solution was extracted with ether. The organic phase was evaporated. 24.1 g of 5-benzyloxy-2-methylpyridine were obtained. The latter was dissolved in 200 ml of glacial acetic acid, mixed with 12 ml of hydrogen peroxide (30%) and refluxed for 2 hours. The mixture was then neutralized with 40% caustic soda solution and 1000 ml of water were added. The solution was extracted with dichloromethane and the organic phase evaporated. 25 g of 5-benzyloxy-2-methylpyridine-N-oxide were obtained.

The latter was dissolved in 90 ml of acetic anhydride and stirring took place for 1 hour at 100° C. After decomposing the excess acetic anhydride with ice, the pH-value of the solution was adjusted to 8 with sodium carbonate and the solution was then extracted with dichloromethane. 25 g of 5-benzyloxy-2-acetoxymethylpyridine were obtained.

The latter was dissolved in 170 ml of methanol and 110 ml of H₂O, mixed with 12 g of NaOH and subsequently refluxed for 4 hours. The solution was then adjusted to a pH-value of 1 and extracted with dichloromethane. The organic phase was discarded and the aqueous phase was adjusted to a pH-value of 8 with sodium carbonate and extracted with dichloromethane. 15.4 g of 5-benzyloxy-2-hydroxymethylpyridine were obtained after evaporating the organic phase.

2.5 g of this substance were dissolved in 100 ml of dichloromethane and mixed with 3 g of activated manganese dioxide and refluxed for 3 hours. The solution was then filtered hot and evaporated and 1.2 g of 5-benzyloxypyridine-2-aldehyde were obtained.

The latter was dissolved in 45 ml of ethanol and 50 ml of water, 1.05 g of 1-hydrazinophthalazine.HCL and 5.3 ml of 1N NaOH were added and the mixture was refluxed for 1 hour. After a short time an orange-yellow substance precipitated, which could be redissolved with 30 ml of ethanol. The solution was filtered hot after adding activated carbon. After cooling, a crystalline substance precipitated, which was recrystallized from ethanol/water.

There was a 0.6 g yield of a yellow substance with a melting point of 162° to 164° C.

EXAMPLE 5

Preparation of 4-methyl-pyridine-2-aldehyde-2'-pyridylhydrazone (PH 22-7)

24.3 ml of 2,4-dimethylpyridine were dissolved in 80 ml of glacial acetic acid, the solution was mixed with 30 ml of 30% hydrogen peroxide and refluxed for 25 hours. The solution was then adjusted to approximately pH 8 with saturated sodium carbonate solution, the solution was extracted with dichloromethane and the organic phase rotated in. The residue was mixed with 90 ml of acetic anhydride and refluxed for 1.5 hours. The pH-value of the solution was adjusted to approximately 8 with 40% NaOH and the solution was extracted with trichloromethane. 30 g of crude 4-methyl-2-acetoxymethylpyridine were obtained.

The latter was dissolved in 150 ml of ethanol, mixed with 7.2 g of NaOH and refluxed for 1 hour. The solution was then filtered, adjusted to pH 2 and extracted with dichloromethane. The organic phase was discarded and the aqueous phase was adjusted with NaOH to pH 8 and extracted with petrol. The organic phase was then again discarded and the aqueous phase extracted with dichloromethane and the extract was rotated in. 7 g of 4-methyl-2-hydroxymethylpyridine were obtained.

The latter was dissolved in 150 ml of trichloromethane, mixed with 8 g of activated manganese dioxide and refluxed for 2 hours. The solution was filtered hot and the filtrate rotated in to dryness. 2.5 g of 4-methyl-pyridine-2-aldehyde were obtained.

1 g of this substance was dissolved in 50 ml of ethanol together with 0.9 g of 2-hydrazinopyridine and refluxed for 1 hour. The solution was then mixed with a little H₂O and cooled. A crystalline substance was obtained, which was sucked off and recrystallized from ethanol/water.

There was a 0.45 g yield of a pale yellow substance with a melting point of 147° to 148° C.

EXAMPLE 6

Preparation of 4-methyl-pyridine-2-aldehyde-1'-phthalazinylhydrazone (PH 22-8)

The reaction took place as in Example 5, with the difference that in the final stage 1 g of 4-methylpyridine-2-aldehyde was dissolved with 1.6 g of 1-hydrazinophthalazine.HCL in 50 ml of 50% ethanol, the solution was mixed with 4 ml of 1N NaOH and refluxed for 1 hour. The solution was then mixed with a little water and cooled. A crystalline substance was obtained, which was recrystallized from ethanol/water.

There was a 0.65 g yield of a yellow substance with a melting point of 208° to 213° C.

EXAMPLE 7

Preparation of 6-chloropyridine-2-aldehyde-2'-pyridylhydrazone (PH 22-11)

4 g of 2-chloro-6-methylpyridine and 9.4 g of m-chloro-peroxybenzoic acid were dissolved in 100 ml of trichloromethane and stirred at room temperature for 5 days. The m-chlorobenzoic acid was filtered off and the filtrate rotated in. The residue was taken up in 250 ml of 4N HCL and extracted with diethyl ether. The aqueous phase was adjusted to approximately pH 8 with sodium hydrogen carbonate and extracted with trichloromethane. The trichloromethane phase was rotated in and 3 g of 2-chloro-6-methylpyridine-N-oxide were obtained as liquid residue.

4 g of this residue were refluxed for 1 hour with 15 ml of acetic anhydride. The reaction solution was added to ice and the pH-value of the sodium carbonate was adjusted to approximately 8. The solution was then extracted with trichloromethane and the extract rotated in. 5 g of the crude ester (2-chloro-6-acetoxymethylpyridine) were obtained.

The latter were refluxed for 2 hours with 1.6 g of sodium carbonate in 30 ml of water and 30 ml of methanol. The solution was then boiled with activated carbon, filtered and firstly extracted with carbon tetrachloride and then trichloromethane. The trichloromethane phase was rotated in and yielded approximately 4 g of 2-chloro-6-hydroxymethyl pyridine.

The latter was dissolved in 100 ml of trichloromethane, mixed with 5 g of activated manganese dioxide and refluxed for 2.5 hours. The manganese dioxide was filtered off hot and the solution rotated in. 2.1 g of 6-chloropyridine-2-aldehyde were obtained.

The latter was dissolved in 30 ml of ethanol, mixed with 1.6 g of 2-hydrazinopyridine, diluted with 20 ml of water and refluxed for 15 minutes. After cooling a crystalline substance was obtained, which was recrystallized from ethanol/water. There was a 0.5 g yield of a pale yellow substance with a melting point of 222° to 225° C.

EXAMPLE 8

Preparation of 5-ethyl-pyridine-2-aldehyde-2'-pyridylhydrazone (PH 22-13)

20 g of 5-ethyl-2-methyl-pyridine were dissolved in 200 ml of glacial acetic acid, mixed with 35 ml of hydrogen peroxide (30%) and stirred for 6 hours at a temperature of 90° to 100° C. The glacial acetic acid was rotated out and the residue was adjusted to pH 8 with sodium carbonate. The weak alkaline solution was extracted with petrol to remove the starting substance. The aqueous phase was then mixed with activated carbon, briefly boiled, filtered hot, cooled and extracted with dichloromethane. There was a 16 g yield of 5-ethyl-2-methyl-pyridine-N-oxide after evaporation.

The latter was stirred with 5 ml of glacial acetic acid and 20 ml of acetic anhydride for 2 hours at 90° to 100° C. The reaction solution was added to ice, neutralized, extracted with dichloromethane and the organic phase was then rotated in. The residue was taken up in an aqueous solution containing 5% by weight of sodium hydrogen carbonate and extracted with diethyl ether. 14 g of 2-acetoxymethyl-5-ethyl pyridine were obtained after evaporating the extract.

The latter was dissolved in 100 ml of 90% ethanol, mixed with 4.1 g of NaOH and then refluxed for 1.5 hours. The solution was then boiled with activated carbon, the excess NaOH was neutralized with 3 ml of glacial acetic acid and then filtered. After rotating in the solution, the residue was taken up with a 5% by weight aqueous sodium hydrogen carbonate solution, extracted with diethyl ether and the organic phase was rotated in.

7 g of 2-hydroxymethyl-5-ethyl pyridine were obtained.

The latter was dissolved in 100 ml of trichloromethane, mixed with 8 g of manganese dioxide and refluxed for 2 hours. The solution was filtered hot and the filtrate rotated in.

4 g of 5-ethyl-pyridine-2-aldehyde were obtained.

2 g of the latter were dissolved in 70 ml of methanol, mixed with 1.2 g of 2-hydrazinopyridine and refluxed for 1.5 hours. The reaction solution was filtered over charcoal in the hot state and the filtrate mixed with water. After cooling, a crystalline substance precipitated, which was recrystallized from methanol/water.

There was a 0.35 g yield of a pale yellow substance with a melting point of 138° to 140° C.

EXAMPLE 9

Preparation of
5-methyl-pyridine-2-aldehyde-2'-quinolylhydrazone
(PH22-14) 20 g of 2,5-dimethylpyridine were dissolved in 100 ml of glacial acetic acid and then stirred for 5 hours at 80° to 90° C. with 35 ml of 30% $H_2O_2$. The excess glacial acetic acid was rotated out and the solution adjusted to pH 8 with 20% NaOH. After extracting with petrol and discarding the organic phase, the solution was extracted with dichloromethane and the organic phase rotated in. 12 g of 2,5-dimethylpyridine-N-oxide were obtained.

The latter was stirred with 20 ml of acetic anhydride for 10 hours at 55° to 75° C. The acetic anhydride was subsequently decomposed with water and the acetic acid formed adjusted to pH 8 with 10% by weight $Na_2CO_3$ solution. The solution was then extracted with dichloromethane and the organic phase rotated in. 13 g of 2-acetoxymethyl-5-methyl pyridine were obtained.

The latter were dissolved in 90% methanol and refluxed for 6 hours after mixing with 4.7 g of NaOH. The solution was then adjusted to pH 7 with hydrochloric acid and extracted with dichloromethane. The organic phase was rotated in and 8.5 g of 2-hydroxymethyl-5-methyl pyridine were obtained.

The latter was dissolved in 150 ml of dichloromethane and, after mixing with 8 g of active $MnO_2$, was refluxed for 7.5 hours. The solution was filtered hot and the filtrate rotated in. 7 g of 5-methyl-pyridine-2-aldehyde were obtained.

0.8 g of the latter was dissolved with 1 g of 2-hydrazinoquinoline in 20 ml of methyl alcohol/water (1:1) and refluxed for 2 hours. The solution was then filtered in the hot state with activated carbon and mixed with a little NaOH. The crystals precipitated after cooling were sucked off and recrystallized from methanol/water.

0.37 g of a yellow-brown substance with a melting point of 201° to 204° C. was obtained.

EXAMPLE 10

Preparation of 2-benzoylpyridine-2'-quinolylhydrazone
(PH 22-15)

1 g of 2-benzoyl pyridine and 0.86 g of 2-hydrazinoquinoline were dissolved in 80 ml of 70% methanol and refluxed for 1.5 hours after adding 0.5 ml of glacial acetic acid. The crystals which precipitated after cooling were sucked off and recrystallized from methanol/water.

0.65 g of a yellow-orange substance with a melting point of 137° to 141° C. was obtained.

EXAMPLE 11

Preparation of
5-methyl-pyridine-2-aldehyde-1'-phthalazinylhydrazone (PH 22-16)

The process according to Example 9 was repeated with the difference that in the final stage 0.62 g of 5-methylpyridine-2-aldehyde with 1 g of 1-hydrazinophthalazine. hydrochloride and 5.1 ml of 1N NaOH were dissolved in methanol and refluxed for 2 hours after mixing with a little water.

0.75 g of a yellow substance with a melting point of 207° to 210° C. was obtained.

EXAMPLE 12

Preparation of
4-acetylamino-pyridine-2-aldehyde-2'-pyridylhydrazone (PH 22-17)

4 g of 2-methyl-4-nitropyridine-N-oxide were dissolved in 90 ml of methanol and reduced with 1.2 g of 10% Pd/charcoal and $H_2$. The catalyst was filtered off, and the filtrate rotated in. The residue was boiled with 200 ml of ethyl acetate, filtered hot and the filtrate was mixed with 100 ml of hexane. The crystals precipitated after cooling the solution was sucked off, washed and dried. 3.1 g of 2-methyl-4-aminopyridine-N-oxide were obtained.

6.5 g of the thus obtained 2-methyl-4-aminopyridine-N-oxide were dissolved in 80 ml of acetic anhydride and heated for 3 hours at 80° to 100° C. The excess anhydride was decomposed with ice, the solution adjusted with $Na_2CO_3$ to pH 8 and extracted with dichloromethane. After rotating in the organic phase, 5 g of 2-acetoxymethyl-4-acetylaminopyridine were obtained.

The latter was dissolved in 100 ml of 90% methanol and after mixing with 9.3 g of $Na_2CO_3.H_2O$ was stirred for 17 hours at room temperature. The solution was then neutralized with acetic acid and adjusted to pH 7.5 with $NaHCO_3$. After extracting with ether, part of the 2-hydroxymethyl-4-acetylaminopyridine precipitated and was recovered by suction removal. The aqueous phase was then extracted with ethyl acetate, the organic phase concentrated to a third and the remaining substance precipitated with hexane. Together 2 g of 2-hydroxymethyl-4-acetylaminopyridine were obtained.

2 g of the thus obtained 2-hydroxymethyl-4-acetylaminopyridine were suspended in 400 ml of dichloromethane, mixed with 6 g of $MnO_2$ and refluxed for 26 hours. The $MnO_2$ was then filtered hot and the dichloromethane solution rotated in to dryness. 1.5 g of 4-acetylaminopyridine-2-aldehyde were obtained.

0.75 g of this substance was dissolved in 20 ml of methanol and mixed with 0.5 g of 2-hydrazinopyridine in 10 ml of $H_2O$ and refluxed for 30 minutes. The resulting solution was cooled. The substance which precipitated after cooling was sucked off and dried.

0.9 g of a pale yellow substance with a first melting point of 141° to 143° C. was obtained. After melting, the substance solidified again and had a second melting point at 240° to 242° C.

EXAMPLE 13

Preparation of 4-acetylaminopyridine-2-aldehyde-1'-phthalazinylhydrazone (PH 22-18)

The process according to Example 12 was repeated with the difference that in the final stage 1.2 g of 4-acetylaminopyridine-2-aldehyde with 1.5 g of 1-hydrazinophthalazine.hydrochloride and 7.6 ml of 1N NaOH were dissolved in 50 ml of methanol/$H_2O$ (1:1) and refluxed for 1 hour. After cooling the solution and adding water, a precipitate was obtained, which was removed by suction and recrystallized from methanol/$H_2O$.

1.2 g of a yellow substance with a melting point of 140° to 143° C. was obtained.

EXAMPLE 14

Preparation of 4-acetylaminopyridine-2-aldehyde-2'-quinolylhydrazone (PH 22-19)

The process according to Example 12 was repeated with the difference that in the final stage 0.6 g of 4-acetylaminopyridine-2-aldehyde was dissolved in methanol and after mixing with 0.56 g of 2-hydrazinoquinoline and 50 ml of $H_2O$ was refluxed for 30 minutes. After cooling the solution, a substance precipitated, which was recrystallized from methanol/$H_2O$.

0.8 g of a yellow substance with a first melting point of 150° to 151° C. was obtained. After melting the substance solidified again and had a second melting point at 236° to 240° C.

EXAMPLE 15

Preparation of 4-acetylamino-2-acetylpyridine-1'-phthalazinylhydrazine (PH 22-20)

On the basis of 2-ethylpyridine, 2-ethyl-4-nitropyridine-N-oxide was prepared (in accordance with the synthesis instructions for 2-methyl-4-nitropyridine-N-oxide by E. Ochiai, J. Org. Chem. 1953, (18), p. 534). 4 g of this substance were dissolved in 60 ml of methanol and reduced with 1.2 g of 10% Pd/charcoal and $H_2$. The catalyst was filtered off and the filtrate rotated in.

3.3 g of 4-amino-2-ethylpyridine-N-oxide were obtained.

6.5 g of this substance was stirred with 50 ml of acetic anhydride for 5 hours at 60° to 80° C. After cooling, the mixture was added to ice and neutralized with $Na_2CO_3$. The solution was extracted with dichloromethane and the organic phase rotated in. The residue was dissolved in 70 ml of 80% methanol, mixed with 9 g of $Na_2CO_3$.$H_2O$ and stirred for 20 hours at room temperature. After rotating off the methanol mixing took place with water and extraction took place for 2 days in the extractor with dichloromethane. The organic phase was then rotated in to dryness and residue was recrystallized from ethyl acetate/hexane. 2 g of 2-(1-hydroxyethyl)-4-acetylaminopyridine were obtained.

2 g of this compound were refluxed for 2 hours with 6 g of $MnO_2$ in 200 ml of dichloromethane. After filtering the hot solution, extraction took place with water and the $H_2O$ phase was rotated in to dryness. 1.1 g of 2-acetyl-4-acetylaminopyridine was obtained.

1.1 g of 2-acetyl-4-acetylaminopyridine was dissolved in 20 ml of methanol and mixed with 0.55 g of 1-hydrazinophthalazine.HCl and 2.7 ml of 1N NaOH and 20 ml of $H_2O$, followed by refluxing for 1.5 hours. The crystals which precipitated on cooling were recrystallized from methanol/$H_2O$.

0.35 g of a yellow substance with a melting point of 249° to 253° C. was obtained.

EXAMPLE 16

Preparation of 2-benzoylpyridine-1'-phthalazinylhydrazone (PH 22-22)

1 g of 2-benzoylpyridine, 1.1 g of 2-hydrazinophthalazine.hydrochloride and 5.5 ml of 1N NaOH were refluxed for 3 and a half hours in 60 ml of 70% methanol. The solution was then mixed with activated carbon and filtered hot. The crystals which precipitated after cooling the filtrate were removed by suction and recrystallized from methanol/$H_2O$.

0.45 g of a yellow substance with a melting point of 177° to 179° C. was obtained.

EXAMPLE 17

Preparation of 4-aminopyridine-2-aldehyde-1'-phthalazinylhydrazine (PH 22-23)

0.2 g of PH 22-18 was dissolved in a solution of 50 mg of NaOH in 6 ml of methanol. The solution was left to stand for three days at room temperature, again mixed with 50 mg of NaOH/6 ml of methanol and left to stand for 2 days at room temperature. After adding a little activated carbon, filtration took place and after adding water the substance was precipitated, sucked off and recrystallized from methanol/water.

55 mg of a yellow substance with a melting point of 252° to 255° C. were obtained.

EXAMPLE 18

Preparation of 2-acetyl-4-aminopyridine-1'-phthalazinylhydrazine (PH 22-24)

0.25 g of PH 22-20 were reacted and isolated in the manner described in Example 15.

100 mg of a yellow substance with a melting point of 232° to 234° C. were obtained.

EXAMPLE 19

Preparation of ethyl-2-pyridylketone-1'-phthalazinylhydrazine (PH 22-25)

20 ml of 2-n-propylpyridine were dissolved in 60 ml of glacial acetic acid, mixed with 40 ml of $H_2O_2$ (30%) and stirred for 16 hours at room temperature and 3 hours at 65° C. The acetic acid was then partly rotated out, the residue was adjusted to pH 8 with NaOH (20%), extracted with dichloromethane and the organic phase rotated in to dryness. 20 g of crude 2-propylpyridine-N-oxide were obtained.

19 g of 2-propylpyridine-N-oxide were dissolved in 40 ml of glacial acetic acid/40 ml of acetic anhydride and stirred for 6 hours at 85° C. and 12 hours at ambient temperature. Excess anhydride was decomposed with $H_2O$, the solution was neutralized with $Na_2CO_3$ and extracted with diethyl ether. After rotating in the ether phase, 12 g of 2-(1-acetoxypropyl)-pyridine remained. This product was dissolved in 120 ml of methanol (70%), mixed with 4 g of NaOH and refluxed for 6 hours. After rotating out the methanol mixing took place with water, extraction with diethyl ether and the organic phase was rotated in. 5.4 g of 2-(1-hydroxypropyl)-pyridine were left. 0.5 g of this substance was refluxed for 2 hours with 1 g of $MnO_2$ and 30 ml of dichloromethane. After filtering off the $MnO_2$, rotation in took place to dryness. 0.3 g of ethyl-2-pyridylketone was obtained.

0.8 g of this substance was refluxed for 2 hours in 60 ml of methanol/$H_2O$ (1:1) with 1.16 g of 1-hydrazinophthalazine and 6 ml of 1N NaOH. The solution was mixed with activated carbon, filtered hot and cooled. The product crystallized in the cold.

0.41 g of a yellow substance with a melting point of 143° to 145° C. was obtained.

EXAMPLE 20

Preparation of pyridine-2-aldehyde-6'-chloro-4'-pyrimidylhydrazone (PH 22-26)

12 g of 4,6-dichloropyrimidine were dissolved in 100 ml of methanol, mixed dropwise with 12 ml of hydrazine hydrate (80%) and stirred for 1 hour at room temperature. After sucking off the precipitate and washing with $H_2O$, 10 g of 4-hydrazino-6-chloropyrimidine were obtained.

10 g of this substance were suspended in 130 ml of methanol and 50 ml of dichloromethane, mixed with 8.2 g of pyridine-2-aldehyde and left to stand for 2 hours at room temperature. The precipitating crystals were removed by suction and washed with methanol.

15.1 g of a pale yellow substance with a melting point of 264° to 266° C. were obtained.

EXAMPLE 21

Preparation of pyridine-2-aldehyde-6'-(N-methyl-N-2''-hydroxypropyl)-amino-3'-pyridazinylhydrazone (PH 22-28)

0.45 g of 3-hydrazino-6-(N-methyl-N-2'-hydroxypropyl)-aminopyridazine (L. Dorigotti et al., Arzneim.-Forsch. 34, 876 (1984)) were dissolved in 10 ml of methanol and mixed with 0.28 g of pyridine-2-aldehyde. After stirring for 2 hours at room temperature, rotation in to dryness took place and followed by recrystallization from methanol/water.

0.36 g of a yellow substance with a melting point of 208° to 210° C. was obtained.

EXAMPLE 22

Preparation of pyridine-2-aldehyde-6'-chloro-2'-pyridylhydrazone (PH 22-29)

2 g of 2,6-dichloropyridine were dissolved in 60 ml of methanol and mixed with 10 ml of 80% hydrazine hydrate. The solution was firstly stirred for 3 days at room temperature and then refluxed for 10 days. Rotation in took place, the residue was taken up with methanol, followed by rotation in again and finally recrystallization from methanol/water. 0.25 g of 2-hydrazino-6-chloropyridine was obtained.

0.25 g of this substance was dissolved in 20 ml of methanol, mixed with 0.187 g of pyridine-2-aldehyde and left to stand for 6 hours at room temperature. The product was completely crystallized out after adding $H_2O$. The substance was sucked off, washed with $H_2O$ and recrystallized from methanol/$H_2O$.

0.25 g of a pale yellow substance with a melting point of 211° to 215° C. was obtained.

EXAMPLE 23

Preparation of pyridine-2-aldehyde-5'-chloro-2'-pyridylhydrazone (PH 22-30)

5 g of 2,5-dichloropyridine were reacted in the manner described in Example 22 with 2.2 ml of hydrazine hydrate. 1.6 g of 2-hydrazino-5-chloropyridine were obtained.

0.7 g of this substance was reacted with 0.52 g of pyridine-2-aldehyde, in the manner described in Example 22.

0.9 g of a pale yellow end product with a melting point of 204° to 206° C. was obtained.

EXAMPLE 24

Preparation of 2-acetylpyridine-6'-chloro-2'-pyrimidylhydrazone (PH 22-32)

1 g of 6-chloro-4-hydrazinopyrimidine according to Example 20 was dissolved in 100 ml of methanol, mixed with 0.83 g of 2-acetylpyridine and stirred at ambient temperature for 18 hours. The solution was rotated in to approximately ⅓ of the volume and the product was precipitated with $H_2O$, sucked off and recrystallized from methanol/water.

1.6 g of a pale yellow substance with a melting point of 145° to 148° C. was obtained.

EXAMPLE 25

Preparation of 5-ethylpyridine-2-aldehyde-6'-methoxy-4'-pyrimidylhydrazone (PH 22-33)

3 g of 4,6-dichloropyrimidine were dissolved in 30 ml of dried methanol and mixed dropwise at −10° C. with a solution of 0.46 g of sodium in 20 ml of dried methanol and stirred at −10° C. for 5 hours and at room temperature for 12 hours. The solution was rotated in, the residue taken up with 50 ml of dichloromethane and a little activated carbon was added. After filtration, rotation in to dryness took place. The initially liquid residue became crystalline solid when left to stand. 2.5 g of 4-chloro-6-methoxypyrimidine were obtained.

2.5 g of this substance were dissolved in 15 ml of methanol, mixed with 6 ml of 80% hydrazine hydrate and refluxed for 1 day. Following rotation in, taking up took place with a little water, adjustment to pH 10 with 1N NaOH and extraction with dichloromethane. The organic phase was concentrated to dryness. 0.92 g of 4-hydrazino-6-methoxypyrimidine was obtained.

0.9 g of this substance was dissolved in 70 ml of ethanol and mixed with 0.96 g of 5-ethylpyridine-2-aldehyde according to Example 18 and a few drops of glacial acetic acid and was refluxed for 0.5 hours. After cooling, the volume was rotated in to half and the product precipitated with $H_2O$ and recrystallized from ethanol/water.

0.5 g of a yellowish-brown substance with a melting point of 190° to 192° C. was obtained.

EXAMPLE 26

Preparation of 2-acetylpyridine-4'-quinazolylhydrazone (PH 22-34)

9.2 g of 4-hydrazinoquinazoline were dissolved in 500 ml of methanol, mixed with 6.9 g of 2-acetylpyridine and refluxed for 2 hours. After cooling the product was precipitated with water and recrystallized from methanol/water.

14 g of a yellow substance with a melting point of 198° to 199° C. were obtained.

EXAMPLE 27

Preparation of 2-acetylpyridine-6'-chloro-4'-pyrimidyl-($N_1$-methyl)-hydrazone (PH 22-35)

1.2 g of 6-chloro-4-(1-methyl-hydrazino)-pyrimidine (cf. PH 22-36) were dissolved in 30 ml of methanol and mixed with 0.92 g of 2-acetylpyridine in 20 ml of methanol. Following vigorous stirring, it was left to stand for 2 days in the dark at room temperature and was then refluxed for 2 days. The solution was then concentrated to approximately 50% of the volume and mixed with water. The precipitated crystals were recrystallized from methanol/$H_2O$.

0.43 g of a pale yellow substance with a melting point of 111° to 114° C. was obtained.

EXAMPLE 28

Preparation of pyridine-2-aldehyde-6'-chloro-4'-pyrimidyl-($N_1$-methyl)-hydrazone (PH 22-36)

2 g of 4,6-dichloropyrimidine were dissolved in 30 ml of methanol, mixed with 1.37 g of triethylamine and 0.63 g of methyl hydrazine and stirred for 2 days at room temperature. 0.1 ml of methyl hydrazine and 0.2 ml of triethylamine were then added and stirred for 4 days at room temperature. After rotating out the solvent, a residue of 2.4 g of crude 6-chloro-4-(1-methylhydrazino)-pyrimidine were obtained, which was immediately processed further.

1.2 g of this substance was dissolved in 30 ml of methanol and mixed with 0.82 g of pyridine-2-aldehyde in 20 ml of methanol. The solution was left to stand in the dark for 3 days at room temperature and then concentrated to ⅓ of the volume. The precipitated crystals were recrystallized from methanol/$H_2O$. 0.35 g of a pale yellow substance with a melting point of 182° to 185° C. was obtained.

The microorganism strains used in the following examples have been filed under the numbers given in the collection of strains of the Borstel Research Institute, Parkallee 1 - 42, 2061 Borstel.

EXAMPLE 29

The acute toxicity after a single administration of PH 22, pyridine-2-aldehyde-thiosemicarbazone (Py-2-TSC), as well as Conteben (thiacetazone, 4-acetylaminobenzaldehyde-thiosemicarbazone) was determined according to H. J. Hapke, Toxikologie für Veterinärmediziner, F. Enke Verlag, Stuttgart 1975. The test animals used were Wistar rats and NMRI white mice. The observed toxicities were compared with data appearing in the literature and given in Table 1 herein before. No toxic effects were observed following a 12 months administration of PH 22-26 (0.1% in the feed) during a therapy test for leprosy-infected mice (cf. Table 17) (weight constancy).

EXAMPLE 30

Proving the inhibiting action of the inventive substances against mycobacteria

The minimum inhibiting concentration of the commercially available and inventive substances given in Table 2 was determined according to the known standard process ("Methods for sensitivity testing of bacterial infectious germs", DIN 58940, part 5).

The determination was carried out on the following bacterial cultures:
1. Mycobacterium lufu (F. Portaels, Annls, Soc. belg. Med. trop. 60, 381 (1980)), FIB 1-85 JS
2. Mycobacterium tuberculosis H 37 RV, FIB 2-85 JS
3. Mycobacterium marinum SN 1254, FIB 3-85 JS
4. Mycobacterium smegmatis ATCC 607 FIB 5-85 JS
5. Mycobacterium avium SN 304 FIB 6-85 JS
6. Mycobacterium avium Patient Strain (Birk) FIB 1-88 JS For culturing the bacterial cultures use was made of nutrient substrates according to Gottsacker and Löwenstein Jensen and culture media according to Lockemann or Dubos-Davis (cf. "Detection processes for mycobacteria from test material, III, culture medium formulations for culturing tuberculosis bacteria", 1978, Publisher: Deutsches Zentralkomitee zur Bekämpfung der Tuberculose, Poppenhusenstrasse 14c, 2000 Hamburg 60).

In each case $5 \times 10^{-3}$ to $5 \times 10^{-5}$ mg, based on the wet weight, of the mycobacterial strains were incubated in 2 ml of culture fluid (Lockemann +0.5 wt/vol. % bovine serum albumen fraction 5) at 31° C. with a graded concentration of the particular inhibitor (dilution series). The culture tubes were read off after 8 to 15 days, as a function of the bacterial strain.

The MIC is the inhibitor concentration in $\mu$Mol/l at which no propagation of the sewn cells is observed.

The results are given in Table 2. They reveal that the inventive compounds have up to more than 200 times greater antimycobacterial activity than the comparison products.

TABLE 2

| Substance | Minimum inhibiting concentration [μM/l] | | | | | |
|---|---|---|---|---|---|---|
| | M. Iufu L 209 | M. tub. H37RV | M. marin. SN1254 | M. smegm. ATCC 607 | M. avium SN 304 | M. avium Patient str. |
| Bactrim | | | | | 32 | >64* |
| Brodimoprim | 80 | 94 | 18 | | — | >100* |
| Streptomycin | — | | — | | 55 | — |
| Kanamycin | | | | | 33 | 17 |
| Rifampicin | | | | | 39 | 5 |
| Conteben | 339 | 4 | | | | 35 |
| Py-2-TSC** | 40 | | | | | |
| PQ | 10 | 28 | 12 | 21 | 24 | |
| PH 22 | 32 | 97 | 77 | 20 | 30 | 29 |
| PH 22-1 | 12,1 | 49 | | 49 | | |
| PH 22-2 | 33 | 48 | 28 | 24 | | 132 |
| PH 22-3 | 6,6 | 31 | 22 | 44 | | 53 |
| PH 22-4 | 6,7 | 4,8 | | 15 | | 58 |
| PH 22-5 | 14,5 | 16,6 | 10,4 | 67 | | |
| PH 22-6 | 5,6 | 8,5 | 7 | 40 | | 7 |
| PH 22-7 | 57 | 113 | 113 | 113 | | |
| PH 22-8 | 31 | 18 | 22 | 44 | | |
| PH 22-9 | 5,5 | 13 | 18,3 | 36,5 | | 73 |
| PH 22-10 | 8,3 | 47 | | 33 | | |
| PH 22-11 | 43 | 86 | | 56 | | |
| PH 22-13 | 53 | 22 | 44 | 22 | | |
| PH 22-14 | 3,8 | 1,2 | 5,7 | 9,5 | | |
| PH 22-15 | 1,2 | 0,97 | 4,6 | 3,1 | | 18,5 |
| PH 22-16 | 4,8 | 1,4 | 76 | 5,7 | | |
| PH 22-17 | 94 | >125 | >125 | >125 | | |
| PH 22-18 | 22,9 | 46 | 92 | 65 | | |
| PH 22-19 | 32,9 | 11,5 | 11,5 | 9,8 | | |
| PH 22-20 | 12,5 | 10,9 | 88 | 15,6 | | |
| PH 22-22 | 2,3 | 18,5 | 10,8 | 12,3 | | 86 |
| PH 22-23 | 26,5 | 13,3 | 38 | 13,3 | | |
| PH 22-24 | 2,2 | 4,5 | 18 | 4,5 | | |
| PH 22-25 | 2,7 | 36 | 101 | 10,8 | | |
| PH 22-26 | 1,3 | 6,2 | 12,9 | 25,7 | | |
| PH 22-27 | 6 | 8,1 | 16,1 | 12,1 | | |
| PH 22-28 | 35 | 140 | 70 | | | |
| PH 22-29 | 3,2 | 1,6 | 6,5 | | | 60 |
| PH 22-30 | 2,7 | 1,3 | 5,4 | | | 13 |
| PH 22-31 | 3,5 | 1,8 | 8,3 | | | 57 |
| PH 22-32 | 1,3 | 6,1 | 28,3 | | | |
| PH 22-33 | 1,5 | 2,4 | 4,9 | | | |
| PH 22-34 | <1,0 | 12 | 64 | | | |
| PH 22-36 | 5,3 | 136 | 119 | | | |
| PH 22-37 | 12,1 | 3 | 6 | 6 | | |

*μg/ml
**Py-2-TSC = Pyridine -2-aldehyde-thio-semicarbazone

EXAMPLE 31

The inhibition of the propagation rate of mycobacterium lufu by PH22, DDS and a combination thereof was determined in the manner described by J. K. Seydel in Chemotherapy 29, 249, 1983.

EXAMPLE 32

Determination of the minimum inhibiting concentration (MIC) of combinations of the inventive compounds with inhibitors of folate synthase and dihydrofolic acid reductase, DNA-synthesis and RNA-synthesis The MIC of the combinations was determined for mycobacterium lufu by chessboard titrations (cf. Behrenbaum M. C., J. Infect. Dis. 137, pp. 122 to 130, 1978 and J. K. Seydel et al, cf. Example 31).

The bacteria were incubated under the conditions according to Example 30.

A two-dimensional dilution series was prepared, the particular components being present in the quantities given in Tables 3 to 15. The results are given in Tables 3 and 15.

The following meanings are used in the Tables:
DDS=4,4'-diaminodiphenylsulphone

K 107=2,4-diamino-5-(4-[2-(4-aminophenyl-4-sulphonylphenyl-amino)-ethoxy]-3,5-dimethoxybenzyl)-pyrimidine K 130=2,4-diamino-5-(4-[3-(4'-aminophenyl-4-sulphonylphenyl-amino)-propoxyl]-3,5-dimethoxybenzyl)pyrimidine Compounds K 107 and K 130 are disclosed in DE-OS 36 03 577.

+++=growth as control
++=slight growth inhibition
+=marked growth inhibition
(+)=almost complete growth inhibition
−=complete growth inhibition

EXAMPLE 33

Proof of the inhibiting action of the inventive substance alone and in combination with respect to M. leprae (in vitro)

The inhibiting action was determined as a reaction of the thymidine absorption and the ATP content in M. Leprae suspensions, in the manner described by A. M. Dhople, Med. Sci. Res., 15, p. 599, 1987. The results are given in Table 16.

EXAMPLE 34

Proof of the therapeutic action of the inventive substances alone and in combination in leprosy-infected mice The therapeutic action was determined as a reduction of the number of acid-resistant bacteria in the mouse paw according to C. C. Shepard, J. Experim. Met., 112, p. 445, 1960.

The results for the monotherapy are given in Table 17 and for the combination in Table 18. It is possible to detect the synergistic effect of the combinations, even under in vivo conditions.

TABLE 3

← PH 22 [μg/ml]

| K 107 [μg/ml] | 16 | 14,4 | 12,8 | 11,2 | 9,6 | 8 | 6,4 | 4,8 | 3,2 | 1,6 | 0 |
|---|---|---|---|---|---|---|---|---|---|---|---|
| 2,4 | | | | | | | | | | − | − |
| 2,16 | | | | | | | | | | − | − |
| 1,92 | | | | | | | | | | − | − |
| 1,68 | | | | | | | | | | − | (+) |
| 1,44 | | | | | | | | | | − | + |
| 1,2 | | | | | | | | | | − | ++ |
| 0,96 | | | | | | | | | | (+) | ++ |
| 0,72 | | | | | | | | | − | + | +++ |
| 0,48 | | | | | | − | − | − | (+) | + | +++ |
| 0,24 | − | − | − | − | − | − | (+) | (+) | + | ++ | +++ |
| 0 | − | − | − | (+) | (+) | + | ++ | +++ | +++ | +++ | +++ |

"M. lufu" L209

TABLE 4

← PH 22 [μg/ml]  5
← K 107 [μg/ml]  1

| DDS [μg/ml] | 0,7 | 0,6 | 0,5 | 0,4 | 0,3 | 0,2 | 0,1 | 0 |
|---|---|---|---|---|---|---|---|---|
| | 0,14 | 0,12 | 0,1 | 0,08 | 0,06 | 0,04 | 0,02 | 0 |
| 0,09 | | | | | | | | − |
| 0,0075 | | | | | | | | − |
| 0,006 | | | | | | | | − |
| 0,0045 | | | | | | | − | ++ |
| 0,003 | | | | | | | − | +++ |
| 0,0015 | | | | | | − | + | +++ |
| 0 | − | − | (+) | (+) | + | ++ | +++ | |

M. lufu L 209

TABLE 5

← PH 22-26 [μg/ml]

| DDS [μg/ml] | 0,8 | 0,7 | 0,6 | 0,5 | 0,4 | 0,3 | 0,2 | 0,1 | 0 |
|---|---|---|---|---|---|---|---|---|---|
| 0,015 | | | | | | | | | − |
| 0,0135 | | | | | | | | | − |
| 0,012 | | | | | | | | − | + |
| 0,0105 | | | | | | | | − | ++ |
| 0,009 | | | | | | | | − | ++ |
| 0,0075 | | | | | | | | − | +++ |
| 0,006 | | | | | | | | − | ++ |
| 0,045 | | | | | | | − | (+) | +++ |
| 0,003 | | | | | | | | + | +++ |
| 0,0015 | | − | − | − | − | − | | ++ | +++ |
| 0 | − | − | (+) | + | ++ | ++ | +++ | +++ | |

M. lufu L209

TABLE 6

← PH 22 [μg/ml]

| K 130 [μg/ml] | 10,8 | 9,6 | 8,4 | 7,2 | 6 | 4,8 | 3,6 | 2,4 | 1,2 | 0 |
|---|---|---|---|---|---|---|---|---|---|---|
| 0,35 | | | | | | | | | − | − |
| 0,3 | | | | | | | | | − | (+) |
| 0,25 | | | | | | | | | − | + |
| 0,2 | | | | | | | | | − | ++ |
| 0,15 | | | | | | | | − | (+) | +++ |
| 0,1 | | | | | − | − | − | − | + | +++ |
| 0,05 | | | | | − | (+) | + | + | ++ | +++ |
| 0 | − | (+) | (+) | + | ++ | ++ | ++ | +++ | +++ | |

TABLE 6-continued

← PH 22 [µg/ml]

| 10,8 | 9,6 | 8,4 | 7,2 | 6 | 4,8 | 3,6 | 2,4 | 1,2 | 0 |
|---|---|---|---|---|---|---|---|---|---|

M. lufu L 209

TABLE 7

← PH 22-26 [µg/ml]

| K 130 [µg/ml] ↑ | 0,9 | 0,8 | 0,7 | 0,6 | 0,5 | 0,4 | 0,3 | 0,2 | 0,1 | 0 |
|---|---|---|---|---|---|---|---|---|---|---|
| 1 | | | | | | | | | | − |
| 0,9 | | | | | | | | | | − |
| 0,8 | | | | | | | | | | − |
| 0,7 | | | | | | | | | − | (+) |
| 0,6 | | | | | | | | | − | (+) |
| 0,5 | | | | | | | | | − | + |
| 0,4 | | | | | | | | − | (+) | + |
| 0,3 | | | | | | | | − | (+) | ++ |
| 0,2 | | | | | | | | − | (+) | +++ |
| 0,1 | − | − | − | − | − | − | (+) | ++ | +++ | |
| 0 | | − | + | + | ++ | +++ | +++ | +++ | +++ | |

M. lufu L 209

TABLE 8

← PH 22 [µg/ml]

| 5-F-Uracil [µg/ml] ↑ | 7,2 | 6,4 | 5,6 | 4,8 | 4 | 3,2 | 2,4 | 1,6 | 0,8 | 0 |
|---|---|---|---|---|---|---|---|---|---|---|
| 16 | | | | | | | | | | − |
| 14,4 | | | | | | | | | | − |
| 12,8 | | | | | | | | | − | (+) |
| 11,2 | | | | | | | | | − | + |
| 9,6 | | | | | | | | | − | + |
| 8 | | | | | | | | | − | ++ |
| 6,4 | | | | | | | | | − | ++ |
| 4,8 | | | | | | | | | − | +++ |
| 3,2 | | | | | | | | | − | +++ |
| 1,6 | − | − | − | − | − | − | − | − | − | +++ |
| 0 | − | (+) | (+) | + | + | ++ | ++ | +++ | +++ | |

M. lufu L 209

TABLE 9

← 5-F-Uracil [µg/ml]

| PH 22-26 [µg/ml] ↑ | 16 | 14,4 | 12,8 | 11,2 | 9,6 | 8 | 6,4 | 4,8 | 3,2 | 1,6 | 0 |
|---|---|---|---|---|---|---|---|---|---|---|---|
| 0,4 | | | | | | | | | | | − |
| 0,36 | | | | | | | | | | | − |
| 0,32 | | | | | | | | | | − | (+) |
| 0,28 | | | | | | | | | | − | (+) |
| 0,24 | | | | | | | | | | − | + |
| 0,2 | | | | | | | | | | − | ++ |
| 0,16 | | | | | | | | | | − | ++ |
| 0,12 | | | | | | | | | − | − | +++ |
| 0,08 | | − | − | − | − | − | − | (+) | + | +++ | |
| 0,04 | − | − | − | (+) | (+) | + | + | + | ++ | +++ | |
| 0 | − | − | (+) | (+) | + | + | ++ | +++ | +++ | +++ | |

M. lufu L 209

TABLE 10

← PH 22 [µg/ml]

| | 12 | 10,8 | 9,6 | 8,4 | 7,2 | 6 | 4,8 | 3,6 | 2,4 | 1,2 | 0 |
|---|---|---|---|---|---|---|---|---|---|---|---|
| | | | | | | | | | | − | ++ |
| 100 | | | | | | | | | | − | ++ |
| 90 | | | | | | | | | | − | ++ |
| 80 | | | | | | | | | | − | +++ |

TABLE 10-continued

| Guanazol [µg/ml] | ← PH 22 [µg/ml] | | | | | | | | | | |
|---|---|---|---|---|---|---|---|---|---|---|---|
| | 12 | 10,8 | 9,6 | 8,4 | 7,2 | 6 | 4,8 | 3,6 | 2,4 | 1,2 | 0 |
| 70 | | | | | | | | − | − | | +++ |
| 60 | | | | | | | | − | (+) | + | +++ |
| 50 | | | | | | | | − | (+) | + | +++ |
| 40 | | | | | | | | − | + | ++ | +++ |
| 30 | | | | | | | − | − | + | ++ | +++ |
| 20 | | | | | | − | (+) | (+) | + | ++ | +++ |
| 10 | | | | | | | − | + | + | ++ | +++ |
| 0 | − | − | − | | | | | | | | |

M. lufu L 209

TABLE 11

| Methotrexate [µg/ml] | ← PH 22 [µg/ml] | | | | | | | | | |
|---|---|---|---|---|---|---|---|---|---|---|
| | 10 | 9 | 8 | 7 | 6 | 5 | 4 | 3 | 2 | 1 | 0 |
| 2,50 | | | | | | | | | | | − |
| 2,25 | | | | | | | | | | − | (+) |
| 2,00 | | | | | | | | | | − | + |
| 1,75 | | | | | | | | | | (+) | ++ |
| 1,50 | | | | | | | | | − | + | ++ |
| 1,25 | | | | | | | | − | + | ++ | +++ |
| 1,00 | | | | | | | − | + | ++ | +++ | +++ |
| 0,75 | | | | | | − | + | ++ | ++ | +++ | +++ |
| 0,50 | | | | | − | + | + | ++ | +++ | +++ | +++ |
| 0,25 | | | | − | − | + | ++ | +++ | +++ | +++ | +++ |
| 0 | − | − | − | + | + | + | ++ | +++ | +++ | +++ | |

M. lufu L 209

TABLE 12

| Desferal [µg/ml] | ← PH 22 [µg/ml] | | | | | | | | | |
|---|---|---|---|---|---|---|---|---|---|---|
| | 15 | 13,5 | 12 | 10,5 | 9 | 7,5 | 6 | 4,5 | 3 | 1,5 | 0 |
| 250 | | | | | | | | | | − | + |
| 225 | | | | | | | | | | − | ++ |
| 200 | | | | | | | | | | − | +++ |
| 175 | | | | | | | | | | − | +++ |
| 150 | | | | | | | | | | − | +++ |
| 125 | | | | | | | | | | − | +++ |
| 100 | | | | | | | | | − | + | +++ |
| 75 | | | | | | | | − | + | ++ | +++ |
| 50 | | | | | | | − | (+) | (+) | + | +++ | +++ |
| 25 | | | | | | | − | + | + | ++ | +++ | +++ |
| 0 | − | − | − | − | − | (+) | + | + | ++ | +++ | |

M. lufu L 209

TABLE 13

| Desferal [µg/ml] | ← PH 22 [µg/ml] | | | | | | | | | |
|---|---|---|---|---|---|---|---|---|---|---|
| | 20 | 18 | 16 | 14 | 12 | 10 | 8 | 6 | 4 | 2 | 0 |
| 150 | | | | | | | | | | − | +++ |
| 135 | | | | | | | | | | − | +++ |
| 120 | | | | | | | | | | − | +++ |
| 105 | | | | | | | | | | − | +++ |
| 90 | | | | | | | | | | − | +++ |
| 75 | | | | | | | | | | − | +++ |
| 60 | | | | | | | | | | − | +++ |
| 45 | | | | | | | | | | − | +++ |
| 30 | | | | | | | | | | − | +++ |
| 30 | | | | | | | | | − | − | +++ |
| 15 | − | − | − | − | − | − | − | − | + | ++ | +++ |
| 0 | +++ | +++ | +++ | +++ | +++ | +++ | +++ | +++ | +++ | +++ | |

M.tbc H 37 Rv

TABLE 14

| | ← PH 22-26 [µg/ml] | | | | | | | | | |
|---|---|---|---|---|---|---|---|---|---|---|
| | 0,8 | 0,72 | 0,64 | 0,56 | 0,48 | 0,4 | 0,32 | 0,24 | 0,16 | 0,08 | 0 |
| 0,08 | | | | | | | | | | | − |
| 0,072 | | | | | | | | | | − | (+) |
| 0,064 | | | | | | | | | | − | (+) |

TABLE 14-continued

| Rifampicin [μg/ml] | PH 22-26 [μg/ml] | | | | | | | | | | |
|---|---|---|---|---|---|---|---|---|---|---|---|
| | 0,8 | 0,72 | 0,64 | 0,56 | 0,48 | 0,4 | 0,32 | 0,24 | 0,16 | 0,08 | 0 |
| 0,056 | | | | | | | | | − | (+) | + |
| 0,048 | | | | | | | | | (+) | (+) | + |
| 0,04 | | | | | | | | − | (+) | + | ++ |
| 0,032 | | | | | | | − | (+) | + | + | ++ |
| 0,024 | | | | | | | − | (+) | + | ++ | +++ |
| 0,016 | | | | | | − | − | (+) | + | ++ | +++ |
| 0,008 | − | − | − | − | (+) | + | ++ | ++ | ++ | +++ | +++ |
| 0 | (+) | (+) | + | ++ | +++ | +++ | +++ | +++ | +++ | +++ | |

M.lufu L 209

TABLE 15

| | 8 | 7,2 | 6,4 | 5,6 | 4,8 | 4 | 3,2 | 2,4 | 1,6 | 0,8 | 0 |
|---|---|---|---|---|---|---|---|---|---|---|---|
| 8 | | | | | | | | | | | − |
| 7,2 | | | | | | | | | | | − |
| 6,4 | | | | | | | | | | | − |
| 5,6 | | | | | | | | | | (+) | |
| 4,8 | | | | | | | | | | | + |
| 4 | | | | | | | | | | | ++ |
| 3,2 | | | | | | | | | | | ++ |
| 2,4 | | | | | | | | | | | +++ |
| 1,6 | | | | | | | | | | | +++ |
| 0,8 | | | | | | | | | | | +++ |
| 0 | − | − | − | − | − | − | (+) | (+) | + | ++ | |

M. avium, Patient strain (Birk)

TABLE 16

Effect of active substance combinations on the in vitro propagation of M. leprae.

| Active substance combination (mg/ml) | | | | % Reduction |
|---|---|---|---|---|
| DDS | K-130 | Rifampicin | PH 22-26 | Thymidine incorporation |
| 5 | | | | 0 |
| 10 | | | | 5 |
| | 10 | | | 0 |
| | 20 | | | 65 |
| | | 50 | | 2 |
| | | 100 | | 0 |
| | | | 50 | 30 |
| | | | 100 | 48 |
| 10 | | | 50 | 37 |
| 10 | | | 100 | 57 |
| | 20 | | 50 | 61 |
| | 20 | | 100 | 73 |
| | | 50 | 50 | 34 |
| | | 50 | 100 | 54 |
| | | 100 | 50 | 47 |
| | | 100 | 100 | 65 |

TABLE 17

Inhibiting effect of PH 22-26 on the propagation of M. leprae in mouse paws.

| | M. leprae/paw (× 10⁶) | | |
|---|---|---|---|
| Treatment Time | Control | Treated mice (0.1% in feed) | % Inhibition |
| 4 months | 0.468 | 0.283 | 40 |
| 6.5 months | 1.720 | 0 540 | 69 |
| 8.5 months | 2.978 | 0.684 | 77 |
| 12 months | 3.682 | 0.945 | 74 |

TABLE 18

Inhibiting effect of active substance combinations on the propagation of M. leprae in mouse paws, after therapy for two months (administration in feed)

| DDS | Rifampicin | K-130 | Brodimoprim | PH 22-26 | % Inhibition |
|---|---|---|---|---|---|
| 0.0001% | | | | | 14 |
| | 0.001% | | | | 19 |
| | | 0.01% | | | 56 |
| | | | 0.01% | | 3 |
| | | | | 0.05% | 0 |
| 0.0001% | | | | 0.05% | 8 |
| | | 0.001% | | 0.05% | 38 |
| | | | 0.01% | 0.05% | 5 |
| 0.0001% | | | 0.01% | 0.05% | 10 |
| 0.0001% | | 0.01% | | 0.05% | 81 |
| 0.0001% | 0.001% | | | 0.05% | 86 |

EXAMPLE 35

Determination of the semimaximum inhibiting concentration ($I_{50}$) of typical representatives of the inventive compounds for the growth of parasitic malaria strains:

Indochina W-2
Sierra Leone D-6

The determination took place according to the standard process (cf. WHO determination process).

The results are given in Table 19

TABLE 19

| | Indochina W-2 | | | Sierra Leone D-6 | |
|---|---|---|---|---|---|
| | $I_{50}$ | $I_{90}$ | [μM/l] | $I_{50}$ | $I_{90}$ |
| PQ 22 | 1.1 | 1.7 | | 1.5 | 2 |
| PH 22 | 2 | 2.5 | | 0.3 | 1.3 |
| PH 22-9 | 1.5 | 5.3 | | 1.8 | 2.2 |
| PH 22-11 | 8.9 | 23 | | 13.1 | 25.7 |
| PH 22-12 | 6.3 | 41 | | 1.5 | 4.3 |
| PH 22-17 | 0.5 | 2.3 | | 0.6 | 1.1 |
| PH 22-25 | 0.4 | 0.7 | | 0.3 | 0.45 |
| PH 22-26 | 3.5 | 6.2 | | 2 | 3 |

EXAMPLE 36

The process according to Example 35 was repeated with the difference that the semimaximum inhibiting concentration of combinations of the inventive compound PH 22 with (2), (3) inhibitors of dihydrofolic acid reductase, (4) inhibitors of folate synthase and dihydrofolic acid reductase and (5), (6) inhibitors of DNA-synthesis were determined. The results are given in Table 20.

TABLE 20

| | $IC_{50}$ [ng/ml] in the case of combinations. | |
|---|---|---|
| | Indochina W-2 | Sierra Leone D-6 |
| (1) PH 22 (100%) | 390.1 | 55.6 |
| (2) PH 22 + K-107 81.6% 18.4% | — | 2.2 |
| (3) PH 22 + K-130 | 37.5 | 47 |

TABLE 20-continued

| | IC$_{50}$ [ng/ml] in the case of combinations. | |
|---|---|---|
| | Indochina W-2 | Sierra Leone D-6 |
| 96% 4% | | |
| (4) PH 22 + K 107 + DDS  82.8% 16.6% 0.6% | 89.8 | 9.8 |
| (5) PH 22 + Desferal  28.6% 71.4% | 146.4 | — |
| (6) PH 22 + 5-F-Uracil  50% 50% | 145.2 | — |

EXAMPLE 37

In vitro determination of the cytostatic activity of typical representatives of the inventive compounds The semimaximum inhibition of cellnumber increase and thymidine incorporation into DNA was determined on the hormone-dependent, human mammary tumour cell line MDA-MB231 (cf. H. D. Soule et al, J. Nat. Cancer Inst., 51, p.1409, 1973) according to the method described by H. Seidenberger, G. Kranzfelder, S. Wappes, H. Schönenberger, W. Beck and M. Girth, Arch. Pharm. 314, 955, 1981 and M. Lippman, M. E. Monaco and G. Bolan, Cancer Res. 37, 1901, 1977. The results are given in Table 21.

TABLE 21

| | 50% Inhibition of cellnumber increase I$_{50}$ μM/l | 50% Inhibition of thymidine incorporation |
|---|---|---|
| PH 22 | 0.151 | 0.118 |
| PQ 22 | 0.321 | 0.157 |
| PH 22-7 | 0.278 | 0.159 |
| PH 22-9 | 0.097 | 0.089 |
| PH 22-12 | 0.46 | 0.33 |
| PH 22-15 | 1.53 | 0.57 |
| PH 22-25 | 0.194 | 0.104 |

We claim:

1. A pharmaceutical composition for the treatment of mycobacterial infections comprising a pharmaceutically acceptable diluent and and effective amount of a substituted 2-acylpyridine-α-(N)-hetarylhydrazones of formula I:

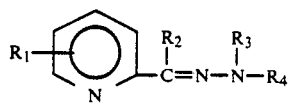

(I)

wherein R$_1$ is hydrogen, halogen, an alkyl group with 1 to 4 C-atoms, a benzyloxy, amino, or acetamino group; R$^2$ is a hydrogen, an alkyl group with 1 to 8 C-atoms, an amino or a phenyl group; R$^3$ is hydrogen or a methyl group; and R$^4$ is a R$_5$ monosubstituted or a 4',5'-benzo fused 3'-pyridazinyl group, R$_5$ being selected from hydrogen, halogen, an alkyl or alkoxy group with 1 to 4 C-atoms, a dialkylamino or substituted dialkylamino group with 1 to 3 C-atoms in the alkyl radicals, as the therapeutically active agent.

2. The composition according to claim 1, in which R$_1$ and R$_2$ are independently amino groups, hydrogen or alkyl groups with 1 to 4 C-atoms.

3. The composition according to claim 1, in which R$_1$ is benzyloxy or an acetamino group.

4. The composition according to claim 1, in which R$_2$ is a phenyl group.

5. The composition according to claim 1, in which R$_5$ is a (N)-methyl-(N)-2-hydroxy-propylamino, methyl, chloro, methoxy or a 4',5'-benzo group.

6. The composition according to claim 1, in which the therapeutically active agent is selected from the group consisting of:
pyridine-2-aldehyde-1'-phthalazinylhydrazone;
2-acetylpyridine-1'-phthalazinylhydrazone;
5-ethylpyridine-2-aldehyde-1'-phthalazinylhydrazone;
5-benzyloxypyridine-2-aldehyde-1'-phthalazinylhydrazone;
4-methylpyridine-2-aldehyde-1'-phthalazinylhydrazone;
5-methylpyridine-2-aldehyde-1'-phthalazinylhydrazone;
4-acetylaminopyridine-2-aldehyde-1'-phthalazinylhydrazone;
4-acetylamino-2-acetylpyridine-1'-phthalazinylhydrazone;
2-benzoylpyridine-2-phthalazinylhydrazone;
4-aminopyridine-1-aldehyde-1'-phthalazinylhydrazone;
2-acetyl-4-aminopyridine-1'-phthalazinylhydrazone;
ethyl-2-pyridylketone-1'-phthalazinylhydrazone;
pyridine-2-aldehyde-6'-(N-methyl-N-2''-hydroxypropyl)-amino-3'-pyridazinylhydrazone.

7. The composition of claim 1, further containing an inhibitor of folate synthetase.

8. The composition of claim 7, in which the folate synthetase inhibitor is a sulphone.

9. The composition of claim 7, in which the folate synthetase inhibitor is a sulphonamide.

* * * * *